United States Patent [19]

Carr, Jr.

[11] Patent Number: 5,118,182

[45] Date of Patent: * Jun. 2, 1992

[54] METHOD FOR DETERMINING FIBRIN FIBER SIZE FROM A SINGLE GEL OPTICAL DENSITY MEASUREMENT

[75] Inventor: Marcus E. Carr, Jr., Richmond, Va.

[73] Assignees: Center for Innovative Technology, Herndon; Virginia Commonwealth University, Richmond, both of Va.

[*] Notice: The portion of the term of this patent subsequent to Apr. 21, 2009 has been disclaimed.

[21] Appl. No.: 593,680

[22] Filed: Oct. 5, 1990

Related U.S. Application Data

[63] Continuation-in-part of Ser. No. 516,426, Apr. 30, 1990.

[51] Int. Cl.$^5$ ............................................. G01N 33/49
[52] U.S. Cl. ................................................... 356/39
[58] Field of Search .......................................... 356/39

[56] References Cited

PUBLICATIONS

Clauss, "Gerinnungsphysiologische Schnellmethode zur Bestimmung des Fibrinogens" *Acta Haematol.* 17:237-246 (1957).
Carr et al., "Mass-Length Ratio of Fibrin Fibers from Gel Permeation and Light Scattering", *Biopolymers*, 16:1-15 (1977).
Carr et al., "Size and Density of Fibrin Fibers from Turbidity", *Marcomolecules*, 13:1473-1477 (1980).
Carr et al., "Dextran-Induced Changes in Fibrin Fiber Size and Density Based on Wavelength Dependence of Gel Turbidity", *Marcomolecules*, 13:1473-1477 (1980).
Carr et al., "The Effect of Dextran 70 on the Structure of Plasma-Derived Fibrin Gels", *J. Clin. Lab. Med.*, vol. 96, No. 6, pp. 985-993 (1980).
Carr et al., "Influence of Ca$^{2+}$ on the structure of repti-lase –derived and thrombin-derived fibrin gels", *Biochem. J.* 239:513-516 (G. Brit.) (1986).
Carr et al., "The Impact of Delayed Fibrinopeptide-A Release on Fibrin Structure", *J. Biol. Chem.*, vol. 262, No. 32, Nov. 15, 1987, pp. 15568-15574.
Carr, "Fluid Phase Coagulation Events Have Minimal Impact on Plasma Fibrin Structure", *Amer. J. Med. Sci.*, vol. 31, No. 5, pp. 433-437 (1988).
Carr et al., "Effect of Glycosaminoglycans on Thrombin- and Antroxin-Induced Fibrin Assembly and Structure", *Thrombosis and Haemostatis*, vol. 62, No. 4, pp. 1057-1061 (1989).
Carr et al., "Effect of Homo Poly(L-amino acids) on Fibrin Assembly: Role of Charge and Molecular Weight", *Biochemistry*, vol. 28, No. 3, pp. 1384-1388 (1989).
Carr et al., "Measurement of Plasma Fibrin Fiber Mass-Length Ratios Utilizing Platelet Aggregometers", *Clinical Research*, vol. 37, No. 2 (Abstract on p. 378A) Apr. 28-May 1, 1989.
Carr et al., "Calculation of Plasma Fibrin Fiber Mass-Length Ratios Utilizing Platelet Aggregometers", *Thrombosis Research*, 59:183-94 (Jul. 1, 1990).

*Primary Examiner*—Vincent P. McGraw
*Attorney, Agent, or Firm*—Whitham & Marheofer

[57] ABSTRACT

Experiments have been conducted which demonstrate that gel optical density is a linear function of the fibrin fiber mass/length ratio ($\mu$) and that the slope of the linear function is dependent on the concentration of fibrinogen in the sample. Once the linear function is known, knowledge of a gel optical density at one wavelength is adequate to determine $\mu$. Such measurements allow quantitative monitoring of fibrin structure, and are clinically relevant.

10 Claims, 3 Drawing Sheets

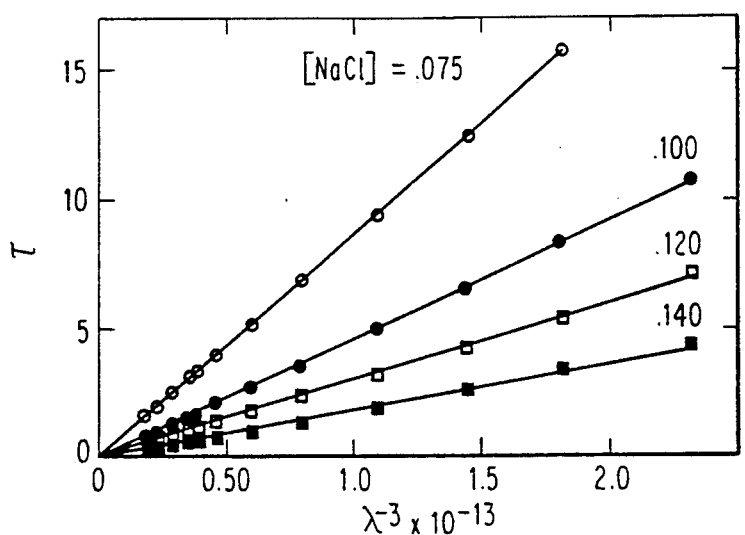
FIG. 1
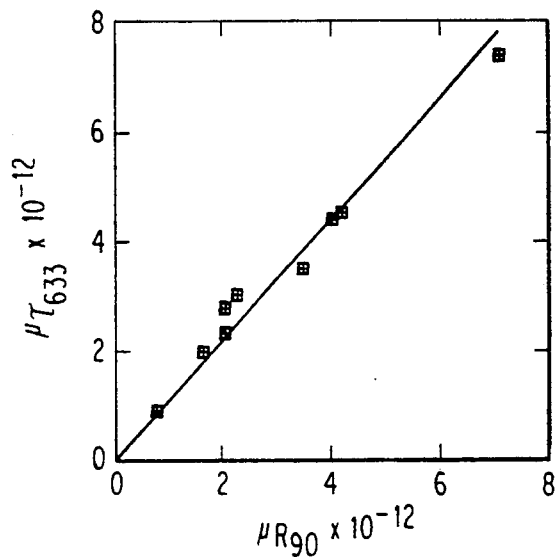
FIG. 2
FIG. 3
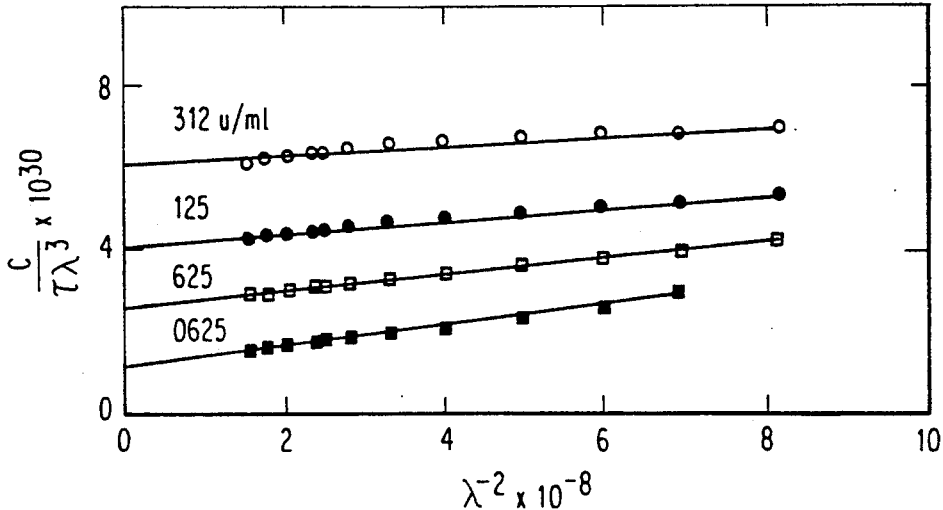

METHOD FOR DETERMINING FIBRIN FIBER SIZE FROM A SINGLE GEL OPTICAL DENSITY MEASUREMENT

CROSS-REFERENCE TO RELATED APPLICATIONS

This patent application is a continuation-in-part (CIP) application of an earlier patent application entitled "Calculation of Plasma Fibrin Fiber Mass/Length Ratio From a Single Measurement of Gel Optical Density", having U.S. Ser. No. 07/516,426, which was filed on Apr. 30, 1990, and that patent application is herein incorporated by reference.

BACKGROUND OF THE INVENTION

1. Field of the Invention

The present invention generally relates to an uncomplicated technique for measuring the size of plasma gel fibers and, more particularly, to a method for determining the fibrin fiber mass/length ratio from a single measurement of gel optical density.

2. Description of the Prior Art

When injury occurs, blood clots to prevent blood loss. Clots contain erythrocytes and platelets but the primary clot scaffolding is interconnected fibrin fibers. Formation of the clot scaffolding is begun by a complex series of proenzyme-enzyme reactions that are initiated upon tissue injury. These reactions result in the conversion of prothrombin into thrombin. Once activated, thrombin cleaves two pairs of small peptides (fibrinopeptides A and B) from the alpha and beta chains respectively of the plasma protein fibrinogen. Once these negatively charged peptides are removed, the repulsive forces that normally prevent fibrinogen aggregation are reduced and new binding sites are exposed. As a consequence, fibrinogen devoid of its fibrinopeptides, termed fibrin monomer, spontaneously assembles into a three dimensional network. This process of polymerization is accomplished by both side-to-side and end-to-end stacking of fibrin monomer units. The initial structure is a long thin protofibrile only two monomer units wide. As the protofibriles reach a critical length, they begin to align themselves along their major axis resulting in larger fibers composed of bundles of protofibriles. A given protofibrile may be involved in one fiber along one portion of its length while being part of another fiber along another portion. As fibers continue to increase in size, virtually all the available fibrin monomer is incorporated into the network. The final result is a space-filling structure composed of fibrin fibers separated by relatively empty spaces. The network is initially stabilized only by hydrogen bonding. The activation of Factor XIII by thrombin permits the introduction of covalent bonds between the monomer units resulting in a network of enhanced strength.

The morphology of fibrin is important to its function. The network can be thought of as a series of interconnecting rods separated by intervening spaces or pores. These pores may be relatively open or may be filled with red cells. The permeability of clots is a function of pore size which can be directly measured by perfusing liquid through a clot. Pore size can also be estimated as a function of fiber size. If the amount of fibrin in a given volume remains constant, pore size will increase as fiber size or mass/length ratio increases. When fibrin is concentrated in a few large fibers, the distances or voids separating them will be increased.

Fiber thickness is determined by the balance of electrochemical forces favoring end-to-end and side-to-side alignment of fibrin monomers during gelation. When end-to-end alignment is favored, long thin fibers are formed. When side-to-side alignment is favored, thick fibers form. Microenvironmental alterations are capable of producing profound effects on fibrin assembly and fiber structure. Low ionic strength, low pH, and the presence of divalent cations favor thick fiber formation. Some cellular release products such as leukocyte cationic protein and platelet factor 4 also favor thick fiber formation. Plasma proteins have variable effects. IgG favors thin fiber formation while albumin has minimal impact. In plasma, the composite of all these influences results in the production of larger fibers than those formed in purified solutions. Causes of altered plasma fibrin fiber structure include: elevated immunoglobulin levels; fibrin polymerization inhibitors such as fibrin degradation products; dysfibrinogenemias—either primary or secondary to hepatic insufficiency; and interference by drugs such as hydroxethylstarch and dextran. Given the dependence of fibrin structure on its microenvironment, additional clot altering variables will undoubtedly be recognized as fibrin structural analysis becomes routinely available.

While normal fibrin structure is obviously critical to clot performance, quantitative measures of fibrin structure have been unavailable. The reporting of plasma clot structure remains a rather qualitative endeavor. Such terms as whispy and flimsy are still used to describe plasma clots which do not appear "normal" in the eye of the technician. Previous attempts to be more quantitative regarding clot structure have centered primarily on elasticity measurements. While intuitively pleasing, a strong clot being better than a weak one, these measurements are not generally available and their interpretation is not routine.

In our laboratory, we have derived methods which allow measurement of gel fiber size. The methods, based on classical light scattering techniques, measure the average mass/length ratio ($\mu$) of the gel fibers. $\mu$ is a measure of fiber size and, if fiber density is uniform, is directly proportional to the second power of the fiber radius. Thus, larger $\mu$ values correlate with larger fiber cross sectional area. While useful in purified protein gel systems, light scattering techniques are not applicable to complex systems such as plasma. To overcome this problem, we modified our procedures to allow measurement of $\mu$ from turbidity. Since turbidity is the sum (integral over all angles) of all scattered light, the value of $\mu$ should be derivable from turbidity measurements. Integration of light scattering equations yielded a new set of equations which predicted that turbidity ($\tau$) would be a reciprocal function of the third power of the wavelength ($\lambda$). The equations indicated that a plot of $\tau$ versus $1/\lambda^3$ would be linear and that the slope of such a plot would be proportional to $\mu$.

The derivation of equations used to calculate the fiber mass/length ratio ($\mu$) from the wavelength dependence of the gel turbidity is as follows:

The turbidity, $\tau$, of a solution is a measure of the decrease in intensity of transmitted light due to scattering and can be calculated by integration of the scattered intensity over all possible angles. For solutions, the scattered intensity depends on the angle, $\theta$, between the primary beam and the scattering direction. Hence, equations (1) and (2) are presented:

$$\tau = 2\pi d^2 (i_\theta/I_o)\sin\theta/d\theta$$

$$i_\theta/I_o = R_{74}(1+\cos^2\theta)/\lambda d^2$$

where $i_\theta$ is the scattered intensity per unit of volume, $I_o$ is the intensity of the incident beam, and d is the distance between scattering volume and detector. The Rayleigh ratio $R_\theta$ depends on the mass and dimensions of the particles. According to theory, for very long and thin rodlike particles, the scattering factor is given by equation (3):

$$R_\theta = cK\lambda\mu/4\pi n\sin(\theta/2)$$

where c is the concentration, $\lambda$ is the wavelength in vacuo, $\mu$ is the mass/length ratio of the fibers (dalton/cm), and n is the refractive index of the solution. The wave vector K is constant for any given wavelength and is given by equation (4):

$$K = 2\pi^2 n^2 (dn/dc)^2/N\lambda^4$$

where dn/dc is the specific refractive index increment of the solute in the solvent and N is Avogadro's number.

It has been shown that equations 2-4 give a good description of experimentally observed light scattering by fibrin fibers. Substituting equations 2 and 3 into equation 1 and integrating, one obtains equation (5):

$$\tau = (44/15)\pi Kc\lambda\mu/n$$

Since K, $\lambda$, and n are known parameters, one can in principle calculate the weight average mass/length ratio of the fibers from the measured turbidity of a gel of known concentration. Equation 5 also implies that the turbidity should vary as $1/\lambda^3$, if we neglect the sight wavelength dependence of n and of dn/dc.

FIG. 1 shows the wavelength dependence of the turbidity of four fibrin gels wherein each gel has fibrin concentration of 1.0 mg/mL and a thrombin concentration of 1.25 NIH units/mL. Each of the gels contains a different concentration of NaCl and was formed directly in polystyrene cuvettes as described below. The prediction that the turbidity should vary as $1/\lambda^3$ is confirmed in FIG. 1, wherein plots of $\tau$ vs $1/\lambda^3$ for fibrin gels formed with varying salt concentrations yields straight line relationships.

FIG. 2 shows a correlation of the mass/length ratios (in daltons/cm) calculated from turbidity and from the 90° scattering intensity, both at 632.8 nm, of a number of fibrin gels. Gels were formed using varying amounts of thrombin to provide a spectrum of $\mu$ values. Mass/length ratios calculated from turbidity are plotted against those calculated from the 90° scattering intensity. The technique of calculating the $\mu$ from a measurement of turbidity is in agreement with the more difficult (and more limited) classical light scattering technique. The excellent agreement for low turbidity gels is obvious.

The turbidity of fibrin gels is proportional to $1/\lambda^3$ over a considerable wavelength range but the proportionality breaks down for gels with very large mass/length ratios ($\mu$). The breakdown occurs because the diameters of fibers with large mass/length ratios ($\mu$) are not small compared with the wavelength of the incident light. Whenever this is the case, the turbidity will not be as large as calculated with equation (5). In these cases the following relation, embodied in equation (6), becomes appropriate:

$$(44/15)\pi Kc\lambda/n\tau = \mu^{-1}(1 + 184\pi^2\sigma^2 n^2/77\lambda^2 \ldots)$$

This result is obtained by integrating a similar expansion for the light scattering intensity in powers of $\sin(\theta/2)/\lambda$. It follows that if one plots $c/\tau\lambda^3$ as a function of $1/\lambda^2$, then the intercept of the plot can be used to calculate the mass/length ratio ($\mu$), while the ratio of the initial slope and the intercept of the plot can be used to calculate the square of an average dimension, $\sigma$ (z-averaged radius of gyration), which is determined by size and shape of the fibers' cross section. This kind of plot if analogous to the plot of $Kc/R_\theta$ vs $\sin^2(\theta/2)$ commonly used to obtain molecular weight and radius of gyration from light scattering of molecularly dispersed particles. For cylindrical fibers of radius $\Gamma$, one may use the series expansion, equation (7), with:

$$\sigma^2 = \Gamma^2/2$$

If one assumes that $1/\tau\lambda^3$ simply varies linearly with $1/\lambda^2$ and neglects higher order terms, the calculated slope will not be seriously in error, as long as no observations are used for which $1/\tau\lambda^3$ is greater than twice its extrapolated value.

FIG. 3 is a plot of $c/\tau\lambda^3$ vs $1/\lambda^2$ for several turbid fibrin gels formed with varying amounts of thrombin (indicated at the left in NIH units/mL). The data have been fitted with straight lines. The intercept of these lines is proportional to the reciprocal of the mass/length ($\mu$) ratio, and the ratio of slope and intercept is proportional to the square of the radius of the fibers. The solutions each contained 1 mg/mL fibrin and 0.1 M NaCl, pH 7.4. The thrombin concentration is indicated by each curve. As predicted, the plots are straight lines. The intercept of these lines is proportional to the reciprocal of the mass/length ($\mu$) ratio, and the ratio of slope and intercept is proportional to the square of the radius of the fibers.

The above confirms the validity of these equations. We have subsequently demonstrated their applicability to plasma systems. We and others have demonstrated the reproducibility of and clinical utility of this parameter in describing patient clot structure. Up to this time, the use of the turbidity technique has been restricted to facilities and laboratories equipped with scanning spectrophotometers. The expense of such equipment has limited the widespread measurement of this useful parameter.

SUMMARY OF THE INVENTION

It is therefore an object of the present invention to provide a method for calculating plasma fibrin fiber mass/length ratios from a single measurement of gel optical density.

According to the invention, we have developed a simple technique for determining $\mu$ from a single measurement of gel optical density. Experiments have been performed which demonstrate that the fiber mass/length ratio is a linear function of turbidity at a given wavelength. Since turbidity is a measure of total scattered light and the amount of scattered light is dependent on the size of the fibers contained in a gel, it is possible to use this linear relationship to determine fiber size in the gel network in terms of the fiber mass/length ratio ($\mu$). Since equipment necessary to perform this measurement is found in most laboratories, this new technique will allow routine measurement of $\mu$. Specifically, the new generation of optical coagulation analyzers can be adjusted to report $\mu$ without additional blood sampling or expense. This would take advantage of the fact that when using solutions of known optical density, arbitrary units can be converted to optical density units. Thus, fiber mass/length ratio, which is rapidly becoming the major clinical quantitative measure of clot structure, should, with this technique, be measurable in most laboratories.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a graph showing the wavelength dependence of the turbidity for four fibrin gels;

FIG. 2 is a graph showing the correlation of the mass/length ratios in daltons/cm calculated from turbidity and from the 90° scattering intensity, both at 632.8 nm, of a number of fibrin gels formed under different conditions;

FIG. 3 is a graph showing the dependence of the turbidity of several fibrin gels with a high mass/length ratio;

DETAILED DESCRIPTION OF A PREFERRED EMBODIMENT OF THE INVENTION

Figure 4:
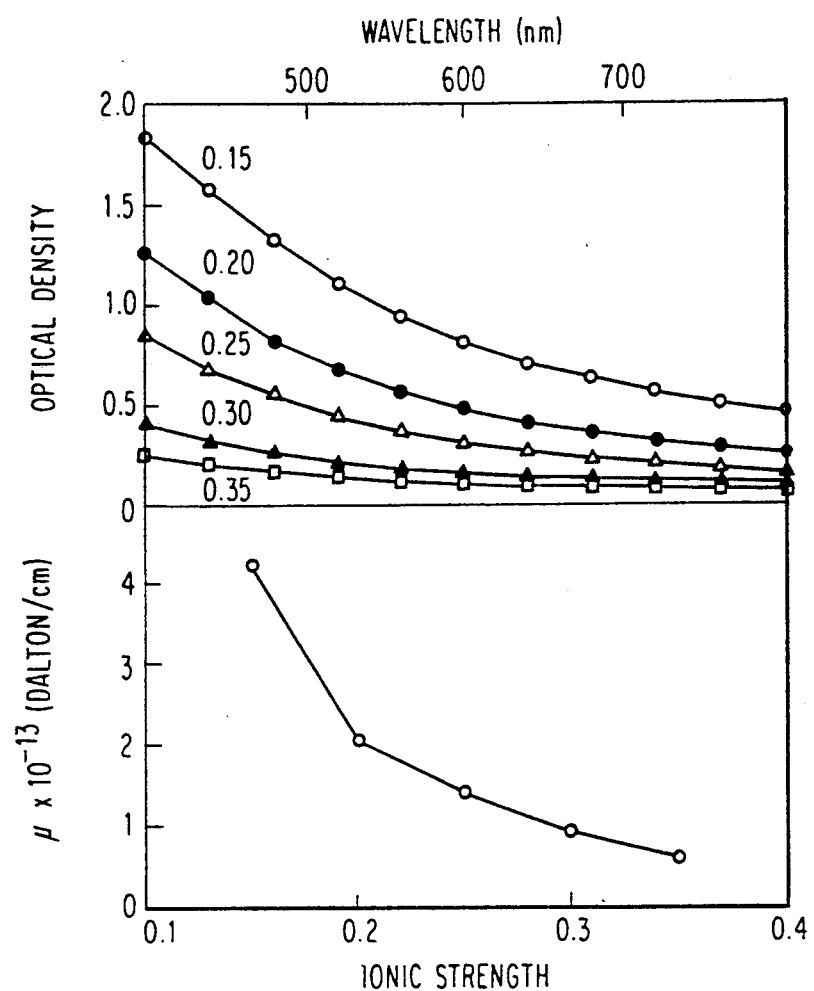
FIG. 4 is a two panel graph showing the effect of ionic strength on plasma gel optical density wavelength dependence in the top panel and showing the fibrin gel fiber size ($\mu$) as a function of ionic strength in the bottom panel.

Experiments have been conducted which demonstrate that fiber mass/length ratio is a linear function of turbidity at a given wavelength. In the experiments, the following materials and methods were used:

Human thrombin, greater than 90% alpha, was purchased as a lyophilized powder from Sigma Chemical Co. (St. Louis, Mo.). The material with a specific activity of 4300 NIH units/mL was dissolved in water, diluted with 0.10 M NaCl to a final concentration of 20 units/mL, divided into 1 mL lots, and frozen at $-90°$ C. Thrombin was free of plasmin and plasminogen. Nanopure water was used in the preparation of all solutions.

Human blood was obtained in citrated glass tubes by sterile venipuncture of normal volunteers. It was spun at low speed to remove large formed elements and then respun at 20,000 g for 20 minutes to remove platelets. Platelet poor plasma was then pooled and frozen at $-30°$ C. Plasma samples were thawed prior to use and brought to room temperature (25° C.) in a thermostated water bath. The fibrinogen concentration of plasma samples was determined by the modified method of Clauss as reported in *Acta Haematol.* 17, 237–246, (1957).

Fibrin gels for turbidity measurements were formed directly in 10 mm polystyrene cuvettes (available from the Fisher Scientific Co.) by mixing platelet poor plasma with buffered solutions of calcium and thrombin (1 NIH unit/mL). Unless otherwise stated, gels were formed at pH 7.4 (0.05 M Tris) and ionic strength 0.15. Added $CaCl_2$ concentration was normally 10 mM.

Turbidity measurements were made at 25° C. with a Cary 2290 scanning spectrophotometer and with a Schimadzu UV-100 UV/Vis recording spectrophotometer (Schimadzu Scientific Instruments, Inc., Columbia, Md.). Kinetic measurements were made at the HeNe laser line, 632.8 nm. The moment of thrombin addition was taken as time zero. Turbidity development was monitored for ten minutes after which time gelation was allowed to go to completion unobserved. After 24 hours, control gels were scanned from 400 to 800 nm and the mass-length ratios of the fibrin fibers were determined according to equation (8):

$$\tau = ((88/15)\pi^3 \, n(dn/dc)^2 C\mu)/N\lambda^3$$

where n is the solution refractive index, dn/dc the refractive index increment, $\lambda$ the wavelength, C the concentration or fibrinogen in g/mL, N Avogadro's number, and $\mu$ the mass-length ratio. For clear gels, $\mu$ was determined from the slope of a plot of $\tau$ versus $1/\lambda^3$. For more turbid gels where the radius of the fibers is no longer small relative to the incident wavelength, $\mu$ was obtained from the inverse of the intercept of a plot of $C/\tau\lambda^3$ versus $1/\lambda^2$.

In the experiments, the size of fibers composing gels of purified and plasma-derived fibrin were determined by scanning the gels from 400 to 800 nm and recording the gel turbidity. Such scans are illustrated in the top panel of FIG. 4 which shows the effect of ionic strength (indicated above each curve) on plasma gel optical density wavelength dependence. The gels utilized in this experiment were formed in the presence of varying amounts of NaCl with all other parameters being identical (i.e., gels were scanned one hour after addition of thrombin 1 NIH units/mL and other clotting conditions included: pH 7.4, 0.05M Tris, fibrinogen 1 mg/ml, and 10 mM $CaCl_2$,). Gels formed at higher ionic strength are clear in appearance and have a low optical density. As ionic strength is decreased, the gel turbidity increases. The increase in gel turbidity is the result of increasing gel fiber size.

In the bottom panel of FIG. 4, the fibrin gel fiber size ($\mu$) is plotted as a function of ionic strength. The mass/length ($\mu$) ratio was calculated as described above from the wavelength dependence of gel optical density. As the ionic strength drops from 0.35 to 0.15, fiber mass-length ratios increase from 0.6 to $4.2 \times 10^{-13}$ daltons/cm.

Figure 5:
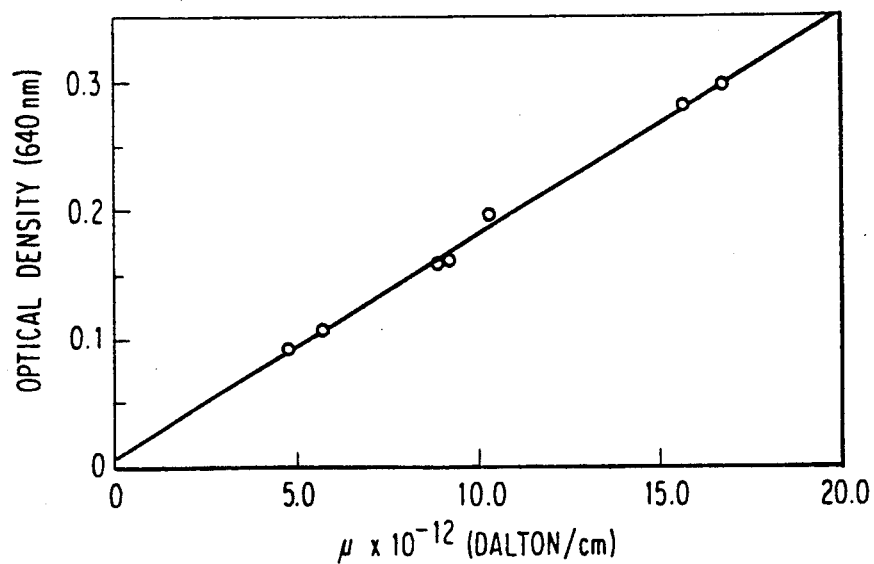
FIG. 5 is a graph showing the correlation of fiber mass/length ratio ($\mu$) with gel optical density at 640 nm.

FIG. 5 shows the correlation of fiber mass/length ratio ($\mu$) with gel optical density at a single optical density (i.e., 640 nm). Since simple spectrophotometers operate at a limited number of wavelengths, it is possible to estimate $\mu$ with these instruments only if changes in $\mu$ are reflected as changes in the optical density at a single wavelength. FIG. 5 confirms that gel optical density at a given wavelength is a linear function of gel fiber size. The gels utilized were formed using varying concentrations of thrombin to yield varying gel fiber size. The values of $\mu$ plotted in FIG. 5 were determined from the wavelength dependence of gel turbidity. Gels were scanned from 400 to 800 nm, plots of gel turbidity versus $1/\lambda^3$ were prepared, and $\mu$ was determined from the slope of plots according to equation (8). The correlation between $\mu$ and optical density at 640 nm is excellent.

Because of the relationship shown in FIG. 5, it is possible for one to determine the mass/length ratio ($\mu$) simply by taking an optical density reading of a plasma sample at 640 nm and determining the corresponding value for $\mu$. The applicant notes that linear relationship would hold true at other wavelengths, e.g., the applicant has confirmed the linear relationship at 400 nm, 626 nm and 945 nm. The applicant anticipates that the novel method may be practiced at any wavelength where a linear curve has been established.

Many of todays automated coagulation analyzers have computer controls. It is anticipated that the curves relating $\mu$ to optical density could be generated and stored in computer memory for any number of wavelengths. Alternatively, values for the mass/length ratio, $\mu$, could be stored in a look up table. All that would be required is for an operator to pick a particular wavelength, make the optical density measurement on a sample, and have the computer find $\mu$ using the stored curve or look up table in the computer.

An implicit assumption of gel structure analysis is that gel formation is complete at the time of mass/length ratio ($\mu$) determination. To assure complete network formation gels could be held for twenty-four hours prior to analysis. However, in clinical laboratories, speed in reporting is crucial, and laboratory tests done entirely by one individual have fewer chances for reporting errors. Therefore, experiments were conducted to determine whether network formation was adequately complete at one hour for $\mu$ determination.

Figure 6:
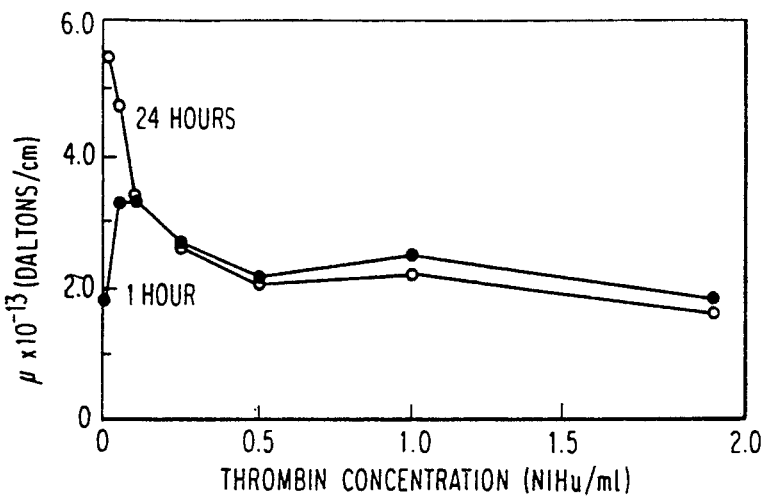
FIG. 6 is a graph showing the effects of time and thrombin concentration on fiber size in purified fibrin gels containing 10 mM $CaCl_2$.

FIG. 6 shows the effect of thrombin concentration on fiber size in purified fibrin gels containing 10 nM $CaCl_2$, where the gels were scanned at one hour and again at twenty-four hours after the addition of thrombin. Below 0.05 NIH units/mL, gel fiber size increased as thrombin activity decreased. Correlation of $\mu$ calculated at one and twenty-four hours was excellent for thrombin concentrations above 0.1 NIH units/ml. Thus plasma clot analysis can be performed one hour after thrombin addition providing adequate initial thrombin concentrations are utilized.

Figure 7:
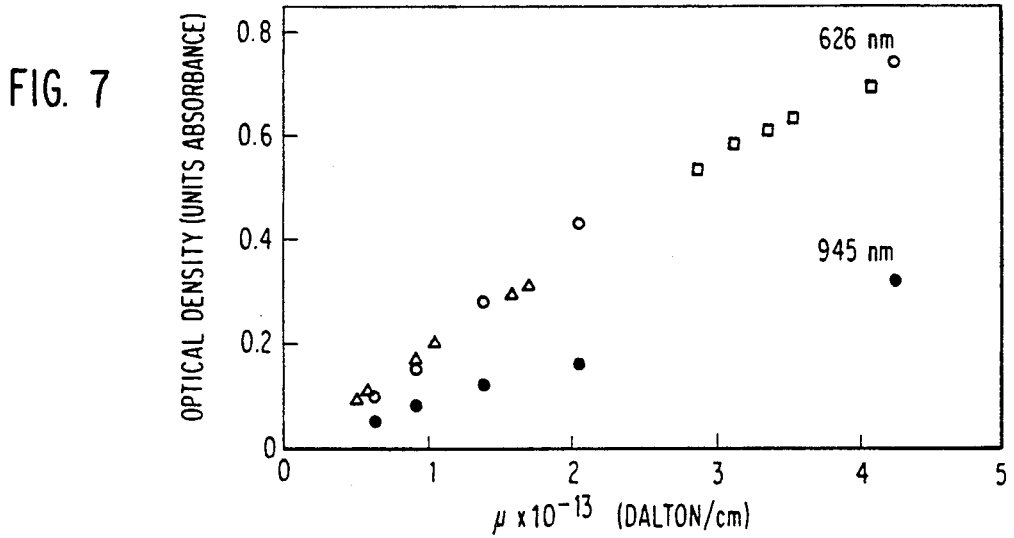
FIG. 7 is a graph showing the correlation of optical density with fiber mass/length ratio ($\mu$) at 626 nm and 945 nm.

FIG. 7 shows the correlation of optical density with fiber mass/length ratio ($\mu$) at two wavelengths: upper curve—626 nm, lower curve 945 nm. Four plasma gels were formed under varying conditions of ionic strength, calcium concentration, and thrombin concentration to yield gels composed of a range of fiber diameter. All four gels contained 1 mg/ml fibrin. The data from all four gels is plotted in FIG. 4. $\mu$ values for the upper three curves are plotted against corresponding optical density at 626 nm. In the bottom curve, $\mu$ is plotted against optical density at 945 nm. For plasma gels, the optical density at both 626 and 945 nm is essentially a linear function of $\mu$.

From FIG. 7, it can be concluded that if a laboratory has a spectrophotometer, even a single wavelength instrument, the laboratory can determine $\mu$. The optical density is measured directly on the spectrophotometer, and $\mu$ is read off a curve such as the one in FIG. 5.

Figure 8:
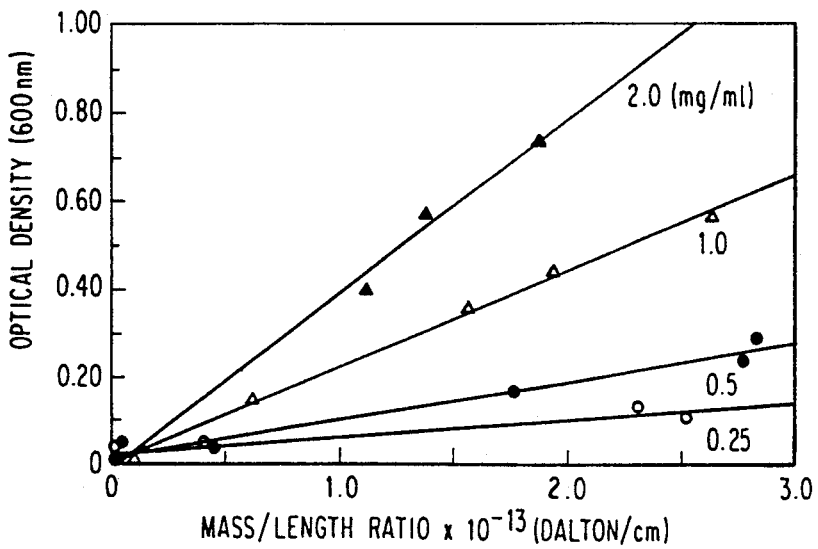
FIG. 8 is a graph showing the correlation of optical density with fiber mass length ratio ($\mu$) for varying fibrinogen concentrations.

FIG. 8 shows the correlation of optical density with the fiber mass/length ratio ($\mu$) for gels with varying concentrations of fibrinogen. The gels with varying concentrations of fibrinogen, e.g., 2.0 mg/l, 1.0 mg/l, 0.5 mg/l and 0.25 mg/l fibrinogen, were prepared simply by diluting a stock fibrinogen in saline solution with Tris buffer and adjusting the ionic strength to 0.15 and the $CaCl_2$ concentration to 10 mM. Fibrinogen in the sample is of course converted to fibrin after the addition of thrombin to the sample. The values of $\mu$ plotted in FIG. 8 were determined from the wavelength dependence of gel turbidity as described above in conjunction with FIG. 5 where the gels were scanned from 400 nm to 800 nm and plots of the gel turbidity versus $1/\lambda^3$ were prepared, and $\mu$ was determined from the slope of plots according to equation (8). FIG. 8 shows that the slope of the line relating optical density to $\mu$ varies as a function of fibrinogen concentration in the gel. For example, a gel optical density of 0.125 corresponds to a $\mu$ ranging from 0.3 to $2.5*10^{13}$ dalton/cm as the fibrin concentration ranges from 2.0 to 0.25 mg/mL.

As described above in conjunction with FIG. 5, a researcher can determine $\mu$ for a gel with a 1.0 mg/ml fibrinogen concentration from a single optical density measurement at 640 nm if he has stored, for later comparison, the curve shown in FIG. 5. FIG. 8 shows that the gel fibrinogen concentration, which can be determined by the modified method of Clauss as reported in *Acta Haematol.* 17, 237–246, (1957) as stated above or by any other suitable method, should be known and adjusted to that for which the curve relating optical density to $\mu$ has been made. The curves relating optical density and $\mu$ can easily be stored in a computer connected to the device which makes the optical density measurements and the comparison can be automatically performed by the computer with the mass/length ratio for the gel on which the optical density measurement was made being displayed to the researcher.

While the invention has been described in terms of a single preferred embodiment wherein a calculation of plasma fibrin fiber mass/length ratio can be made from a single measurement of gel optical density, those skilled in the art will recognize that the invention can be practiced with modification within the spirit and scope of the appended claims.

Having thus described my invention, what I claim as new and desire to secure by Letters Patent is as follows:

1. A method for determining plasma fibrin fiber size from a single optical density measurement, comprising the steps of:
   adjusting a plasma sample to have
   (i) a predetermined fibrinogen concentration ranging from approximately 0.25 mg/ml to physiologic level;
   (ii) an ionic strength of approximately 0.15 M,
   (iii) a thrombin concentration above approximately 0.1 NIH units/ml,
   (iv) a calcium concentration ranging from approximately 5 mM to approximately 10 mM, and
   (v) a pH buffered at a physiologic level;
   measuring an optical density measurement for said plasma sample at a particular wavelength after said step of adjusting said plasma sample; and
   determining a mass/length ratio from said optical density measurement from a predetermined linear function relating optical density to mass/length ratio at said particular wavelength and for said predetermined fibrinogen concentration.

2. A method as recited in claim 1 wherein said predetermined fibrinogen concentration used in said step of adjusting is selected from the group consisting of 0.25 mg/ml, 0.5 mg/ml, 1.0 mg/ml, and 2.0 mg/ml.

3. A method as recited in claim 1 wherein said step of measuring is performed one hour after said step of adjusting.

4. A method as recited in claim 1 wherein said step of determining is performed using a graph of said linear function.

5. A method as recited in claim 1 wherein said step of determining is performed using a computer look-up table.

6. A method for determining plasma fibrin fiber size from a single optical density measurement, comprising the steps of:
   defining a linear function for a particular wavelength of light which relates mass/length ratio to optical density for fibrin size in a plasma sample clot wherein said plasma sample has
   (i) a predetermined fibrinogen concentration ranging from approximately 0.25 mg/ml to physiologic level;
   (ii) an ionic strength of approximately 0.15 M,
   (iii) a thrombin concentration above approximately 0.1 NIH units/ml,
   (iv) a calcium concentration ranging from approximately 5 mM to approximately 10 mM, and
   (v) a pH buffered at a physiologic level, prior to clotting;
   storing said linear function;
   adjusting a plasma sample to be measured to have an equivalent predetermined fibrinogen concentration, ionic strength, thrombin concentration, calcium concentration and pH to that used in said determining step;
   measuring an optical density measurement for said plasma sample to be measured at said particular wavelength after said step of adjusting said plasma sample to be measured; and
   determining a mass/length ratio from said optical density measurement from said stored linear function.

7. A method as recited in claim 6 wherein said predetermined fibrinogen concentration used in said steps of defining and adjusting is selected from the group consisting of 0.25 mg/ml, 0.5 mg/ml, 1.0 mg/ml, and 2.0 mg/ml.

8. A method as recited in claim 6 wherein said step of measuring is performed one hour after said step of adjusting.

9. A method as recited in claim 6 wherein said step of determining is performed using a graph of said linear function.

10. A method as recited in claim 6 wherein said step of determining is performed using a computer look-up table.

* * * * *